(12) United States Patent
Berge

(10) Patent No.: US 6,417,232 B1
(45) Date of Patent: Jul. 9, 2002

(54) FATTY ACID ANALOGUES FOR THE TREATMENT OF PRIMARY AND SECONDARY RESTENOSIS

(75) Inventor: Rolf Berge, Bønes (NO)

(73) Assignee: Thia Medica AS (NO)

( * ) Notice: Subject to any disclaimer, the term of this patent is extended or adjusted under 35 U.S.C. 154(b) by 0 days.

(21) Appl. No.: 09/674,982

(22) PCT Filed: May 7, 1999

(86) PCT No.: PCT/NO99/00149

§ 371 (c)(1),
(2), (4) Date: Jan. 8, 2001

(87) PCT Pub. No.: WO99/58123

PCT Pub. Date: Nov. 18, 1999

(30) Foreign Application Priority Data

May 8, 1998 (WO) .............................. PCT/NO98/00143

(51) Int. Cl.⁷ ..................... A61K 31/22; A61K 31/19; A61K 31/20

(52) U.S. Cl. ..................... 514/546; 514/557; 514/558; 514/550

(58) Field of Search ............................... 514/546, 550, 514/557, 558

(56) References Cited

U.S. PATENT DOCUMENTS 5,827,645 A * 10/1998 Sundrehagen .................. 435/4
6,046,237 A * 4/2000 Berge et al. ................. 514/546
6,197,789 B1 * 3/2001 Grainger et al. ............ 514/319

FOREIGN PATENT DOCUMENTS

EP 0345038 11/1993
WO WO 97/03663 2/1997

OTHER PUBLICATIONS

Asiedu et al. (1996), "Long–term Effect of Tetradecylthioacetic Acid: A Study on Plasma Lipid Profile and Fatty Acid Composition and Oxidation in Different Rat Organs," *Biochimica et Biophysica Acta* 1300:86–96.

Dyroy et al. (1999), "The Influence of a Novel Antioxidant Fatty Acid on the Development of Stenosis After Balloon Injury," *Lipids* 34:S339.

* cited by examiner

*Primary Examiner*—Zohreh Fay
*Assistant Examiner*—Brian-Yong Kwon
(74) *Attorney, Agent, or Firm*—Reed & Associates

(57) ABSTRACT

The present invention relates to novel fatty acid analogues of the general formula (I): $CH_3-[CH_2]_m-[X_i-CH_2]_n-COOR$, wherein n is an integer from 1 to 12, and wherein m is an integer from 0 to 23, and wherein i is an odd number which indicates the position relative to COOR, and wherein $X_i$ independent of each other are selected from the group comprising O, S, SO, $SO_2$, Se and $CH_2$, and wherein R represents hydrogen or $C_1-C_4$ alkyl, with the proviso that at least one of the $X_i$ is not $CH_2$, or a salt, prodrug or complex thereof, for the preparation of a pharmaceutical composition for the treatment and/or prevention of primary and/or secondary stenosis. Further the present invention relates to the use of said compounds for the prevention and/or treatment of a disease caused by procedural vascular trauma and/or pathological proliferation of smooth muscle cells, and/or an increased level of plasma homocysteine.

19 Claims, 3 Drawing Sheets

FATTY ACID ANALOGUES FOR THE TREATMENT OF PRIMARY AND SECONDARY RESTENOSIS

CROSS-REFERENCE TO RELATED APPLICATIONS

This application claims priority under 35 U.S.C. §120 to PCT No. PCT/NO99/00149, filed May 8, 1999.

BACKGROUND OF THE INVENTION

The present invention relates to novel fatty acid analogues which can be used for the treatment and/or prevention of primary and secondary stenosis. Further, the present invention relates to the use of said analogues for the treatment of diseases caused by procedural vascular trauma, and more specifically the invention relates to conditions associated with smooth muscle cell proliferation.

Many pathological conditions have been found to be associated with smooth muscle cell proliferation. Such conditions include restenosis, atherosclerosis, coronary heart disease, thrombosis, myocardial infarction, stroke, smooth muscle neoplasms such as leiomyoma and leiomyosarcoma of the bowel and uterus and uterine fibroid or fibroma.

Over half a million interventional intravascular procedures are performed each year. While such invasive procedures continue to improve over time, as many as 30–50% of the procedures performed each year fail as a result of restenosis, i.e. the formation of secondary stenosis. The reduction of restenosis is, therefore, often cited as the most critical factor in increasing the success realised in the treatment of cardiovascular disease through the use of interventional intravascular procedures, such as angioplasty, atherectomy, and procedures utilising stents and laser technology.

In balloon angioplasty, e.g. Percutaneous Transluminal Coronary Angioplasty (PTCA), a small incision is made to an artery in the patient's leg or arm and a long hollow tube, called a guide catheter, is inserted into the artery. A thick guide wire and deflated balloon catheter are then inserted into the guide catheter and are carefully advanced through the patient's blood vessels using x-ray visualisation. The deflated balloon is advanced until it reaches the site of the luminal narrowing, at which point the physician inflates the balloon one or more times to a pressure of about 4–6 atm for about 60 sec. When inflated, the balloon cracks and fractures the plaque and stretches the muscle fibre in the artery wall beyond its ability to recoil completely. Although no plaque is removed in this procedure, the fracturing of the plaque and the stretching of the arterial wall increase the vessel lumen, thereby allowing for increased blood flow.

The restenosis that accompanies such procedures is characterised by platelet aggregation and adhesion, smooth muscle cell proliferation, narrowing of the vessel lumen, restricted vasodilatation, and an increase in blood pressure. Smooth muscle cells in the intimal layer of the artery have been reported to enter the growth cycle within about 2–3 days of these procedures and to proliferate for several days thereafter (intimal hyperplasia).

Compounds that reportedly suppress smooth muscle proliferation in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation.

As is apparent from the foregoing, many problems remain to be solved in the use of inhibitory drugs to effectively treat smooth muscle cell mobilisation and proliferation. It would be highly advantageous to develop new compositions or methods for inhibiting stenosis, restenosis or related disorders due to proliferation and mobilisation of vascular smooth muscle cells following, for example, traumatic injury to vessels rendered during vascular surgery.

Treatment with modified fatty acids represent a new way to treat these diseases.

EP 345.038 and PCT/NO95/00195 describes the use of non-β-oxidizable fatty acid analogues for the treatment of hyperlipidemic conditions.

It has now been found that these fatty acid analogues have broader area of applications.

Further, we have now synthesised and characterised novel fatty acid analogues.

In feeding experiments with the fatty acid analogues of the present invention, the results show that these compounds lower the adipose tissue mass and body weight, and are thus potent drugs for the treatment of obesity and overweight. These results are described and claimed in the Applicants co-pending application PCT/NO99/00135.

We have also shown that the fatty acid analogues are potent antidiabetic compounds, with a profound effect on the levels of glucose and insulin. These results are described and claimed in the Applicants co-pending application PCT/NO99/0136.

We have shown that the compounds of the present invention inhibit the formation of secondary stenosis, and the present application thus relates to the use of these compounds for the prevention and/or treatment of restenosis. Further, we have shown that the compounds inhibit the proliferation and mobilisation of smooth muscle cells, and lower the concentration of plasma homocysteine. It is thus anticipated that the compounds also will have a preventive and/or therapeutic effect on primary stenosis. Further, it is anticipated that the present compounds will be useful for the treatment and/or prevention of atherosclerosis, coronary heart disease, thrombosis, myocardial infarction, stroke and smooth muscle cell neoplasms, and also diseases caused by procedural vascular trauma.

The novel compounds of the present invention are characterised by minor modifications of the natural fatty acids. Sulphur, selenium or oxygen are preferably substituted for one or more of the carbons in the fatty acid backbone. The compounds defined by the formula I have properties which give them a unique combination of biological effects.

Tetradecylthioacetic acid (TTA) and tetradecylselenioacetic acid (TSA) are most thoroughly studied, and we have shown several beneficial effects in various model animal systems.

The studies have shown that TTA has properties very similar to natural fatty acids, the main difference being that TTA is not oxidised by the mitochondrial β-oxidation system. However, the presence of compounds of the present invention have been shown to increase the β-oxidation of other (non-substituted) fatty acids.

Administration of TTA to rats for 12 weeks nearly doubled the hepatic and plasma content of monounsaturated fatty acids (mainly oleic acid), while polyunsaturated fatty acids (mainly linoleic acid and DHA) decreased. Thus the compound of the present invention modifies the composition of the lipids in various tissues.

Feeding moderate doses of TTA to animals like rats, mice, rabbits and dogs decreased both plasma cholesterol and triacylglycerol levels within days of treatment. We have also shown the same effect for TSA, and compounds of the present invention with Sulphur substituted in positions 5 or 7 have been shown to increase the β-oxidation, and it is thus anticipated that also these fatty acid analogues will lower the plasma levels of triacylglycerols and cholesterol. TTA and TSA are far more potent in this respect than polyunsaturated fatty acids like EPA.

The experimental data of the present invention have unexpectedly revealed that the formation of secondary stenosis (restenosis) after angioplasty is markedly reduced or inhibited in various model animals given the compounds of formula I either orally or locally. This is clearly demonstrated in the experimental section, examples 3 and 4, which demonstrates that the artery diameter, several weeks after the angioplasty procedure, is maintained for animals given TTA, while the diameter is markedly reduced for control animals. These in vivo results clearly demonstrate the potential of these compounds for the prevention of the formation of secondary stenosis.

The action mechanisms for the formation of restenosis after PTCA are not completely understood, but it have been shown that restenotic lesions has an overgrowth of smooth muscle cells in the intimal layers of the vessel.

We have shown that the compounds of the present invention reduce the growth and mobilisation of smooth muscle cells. Increased smooth muscle cell proliferation has also been associated with atherosclerosis, coronary heart disease, thrombosis, myocardial infarction and stroke.

Normal blood vessels are lined with a layer of endothelial cells. The endothelium releases local factors such as nitric oxide, prostaglandin $I_2$ and prostacyclin into the vessel wall (intramural release) and into the blood stream (intraluminal release). These factors maintain vascular tone (vessel relaxation), inhibit clot formation on the vessel inner surface (platelet adhesion and aggregation), inhibit monocyte adherence and chemotaxis, and inhibit smooth muscle cell migration and proliferation. As a result of this process, vasodilation and thrombolysis occurs, and blood flow is maintained. If the endothelium is dysfunctional or damaged, however, nitric oxide and prostacyclin release is impaired. Platelet aggregation and adhesion can occur unopposed, with platelet-derived products acting directly on the smooth muscle cells to cause vasoconstriction. The net result is a blood vessel which is highly susceptible to thrombosis and vasospasm.

Atherosclerosis can form within a blood vessel over a period of years from a variety of causes. The resulting lesion, or plaque, may progressively occlude the vessel and impede blood flow to vital organs.

The described vasoconstrictive physiologic mechanisms occur both in peripheral and in coronary arteries, but the consequences of the processes are more life threatening in the coronary arteries. Coronary arteries, the arteries of the heart, perfuse the cardiac muscle with oxygenated arterial blood. They provide essential nutrients and allow for metabolic waste and gas exchange. These arteries are subject to unremitting service demands for continuous blood flow throughout the life of the patient. A severe proximal coronary stenosis with endothelial injury induces cyclic coronary flow reductions ("CFR's"). These are periodic or spasmodic progressive reductions in blood flow in the injured artery. Episodes of CFR's are correlated to clinical acute ischemic heart disease syndromes, which comprise unstable angina, acute myocardial infarction and sudden death. The common pathophysiologic link is endothelial injury with vasospasm and/or thrombus formation.

It is thus anticipated and claimed that the compounds of the present invention by its action on the smooth muscle cells will have a favourable effect on the group of diseases mentioned above.

As indicated, the present compounds also exhibit a lipid lowering effect, and the administration of a compound of the present invention is thus the compound of choice for the treatment or prevention of artery related diseases. The low toxicity of these compounds makes them very suitable as prophylactically agents given to mammals in need thereof, e.g. to prevent the formation of primary stenosis.

We have also demonstrated that the compounds of the present invention decrease the plasma concentration of homocysteine. Elevated levels of homocysteine are considered as a risk factor for, and are correlated with the development of atherosclerosis. Thus, based on this homocysteine lowering effect of TTA it is anticipated that the present compounds will have a inhibiting effect on the formation of primary stenosis.

DETAILED DESCRIPTION OF THE INVENTION

The present invention discloses that modified fatty acid analogues at non-cytotoxic concentrations can be used for the treatment and/or prevention of stenosis and restenosis.

We have also shown that the compounds of the present invention reduces the proliferation and mobilisation of smooth muscle cells, and it is known that proliferation of smooth muscle cells is a pathological factor in diseases such as atherosclerosis, coronary heart disease, thrombosis, myocardial infarction, stroke and smooth muscle cell neoplasms, and the treatment and/or prevention of such diseases by the use of the compounds of formula (I) are also part of the present invention.

The present invention relates to the use of fatty acid analogues of the general formula (I):

$$CH_3-[CH_2]_m-[X_i-CH_2]_n-COOR$$

wherein n is an integer from 1 to 12, and
wherein m is an integer from 0 to 23, and
wherein i is an odd number which indicates the position relative to COOR, and
wherein $X_i$ independent of each other are selected from the group comprising O, S, SO, $SO_2$, Se and $CH_2$, and
wherein R represents hydrogen or $C_1-C_4$ alkyl,
with the proviso that at least one of the $X_i$ is not $CH_2$, or a salt, prodrug and complex thereof, for the preparation of a pharmaceutical composition for the treatment and/or prevention of primary and/or secondary stenosis.

In particular, the invention relates to the use of a compound of the general formula I, for the treatment and/or prevention of a disease caused by procedural vascular trauma and/or pathological proliferation of smooth muscle cells and/or an increased level of plasma homocysteine.

Preferred embodiments of the invention relate to the use of a compound of the general formula I, wherein the diseases are selected from the group comprising atherosclerosis, coronary heart disease, thrombosis, myocardial infarction, stroke, vascular dementia and smooth muscle cell neoplasms.

One embodiment of the invention is the use of a compound of formula I wherein $m \geq 13$.

A presently preferred embodiment of the invention comprises the formula I, wherein $X_{i=3}$ is selected from the group consisting of O, S, SO, $SO_2$ and Se, and wherein $X_{i=5-25}$ is $CH_2$.

Tetradecylthioacetic acid (TTA) and Tetradecylselenoacetic acid (TSA), i. e. $X_{i=3}$ is Sulphur and Selenium, respectively are presently preferred compounds.

A further aspect of the invention relates to a method for the prophylactic or therapeutic treatment of primary or secondary stenosis in a mammal, said method comprising the step of administering to a mammal in need thereof an effective amount of fatty acid analogues of the general formula (I):

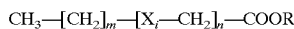

wherein n is an integer from 1 to 12, and wherein m is an integer from 0 to 23, and wherein i is an odd number which indicates the position relative to COOR, and wherein $X_i$ independent of each other are selected from the group comprising O, S, SO, $SO_2$, Se and $CH_2$, and wherein R represents hydrogen or $C_1$–$C_4$ alkyl, with the proviso that at least one of the $X_i$ is not $CH_2$, or a salt, prodrug or complex thereof.

The treatment involves administering to a patient in need of such treatment an effective concentration which is maintained substantially continuously in the blood for the duration of the period of its administration.

Further, the invention relates to a pharmaceutical composition for the prevention and/or treatment of a primary and/or secondary stenosis. Preferably, the pharmaceutical composition comprises in admixture with the fatty acid analogues a pharmaceutically acceptable carrier or excipient.

The invention also relates to novel fatty acid analogues of the formula I

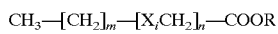

wherein n is an integer from 1 to 12, and wherein m is an integer from 0 to 23, and wherein i is an odd number which indicates the position relative to COOR, and wherein $X_i$ independent of each other are selected from the group comprising O, S, SO, $SO_2$, Se and $CH_2$, and wherein R represents hydrogen or $C_1$–$C_4$ alkyl, with the proviso that at least one of the $X_i$ is not $CH_2$, or a salt, prodrug or complex thereof.

FIGURE LEGENDS

DEFINITIONS

Primary Stenosis

Figure 1:
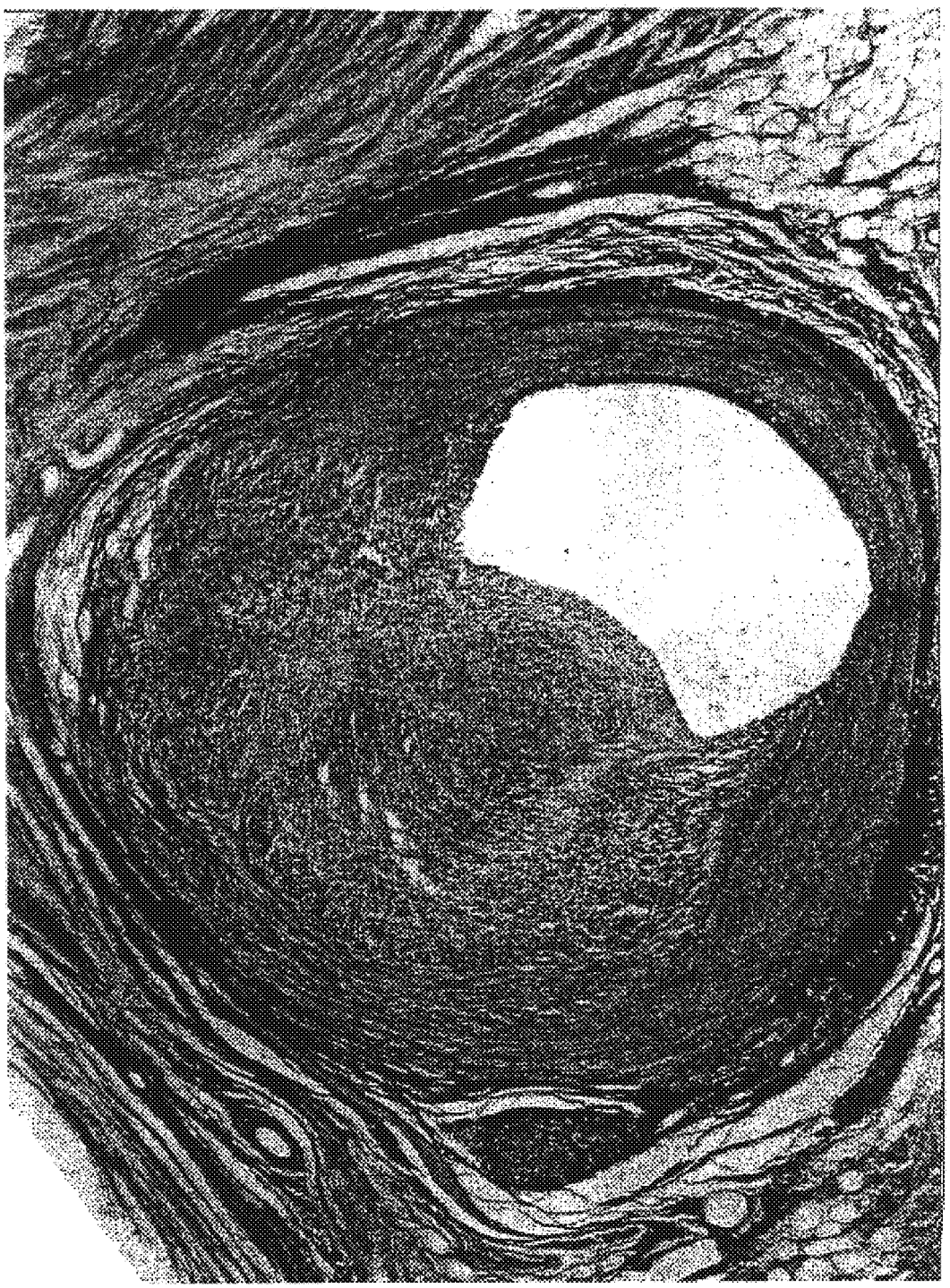
FIG. 1 shows an iliac artery of a control animal, 6 weeks after balloon injury.

The term stenosis refers to a stricture of any canal, and especially a narrowing of one of the cardiac valves. Primary stenosis refers to the formation of stenosis due to a disease condition, e.g. atherosclerosis.

Secondary Stenosis (Restenosis)

The terms <<secondary stenosis>> or <<restenosis>> refers to the recurrence of stenosis after corrective surgery, i.e. narrowing of a structure (usually a coronary artery) following the removal or reduction of a previous narrowing.

Procedural Vascular Trauma

The term procedural vascular trauma refers to conditions caused by vascular surgical procedures such as angioplasty, atheroectomy, placement of stent (e.g. in a vessel), thrombectomy and grafting.

Proliferation

As used herein the term <<proliferation>> means an increase in cell number, i.e. by mitosis of the cells.

ADMINISTRATION OF THE COMPOUNDS OF THE PRESENT INVENTION

As a pharmaceutical medicament the compounds of the present invention may be administered directly to the mammal by any suitable technique, including parenterally, intranasally, orally, or by absorption through the skin. They can be administered locally or systemically. The specific route of administration of each agent will depend, e.g., on the medical history.

Examples of parenteral administration include subcutaneous, intramuscular, intravenous, intraarterial, and intraperitoneal administration.

As a general proposition, the total pharmaceutically effective amount of each of the compounds administered parenterally per dose will preferably be in the range of 5 mg/kg/day to 1000 mg/kg/day of patient body weight, although, as noted above, this will be subject to a great deal of therapeutic discretion. For TTA it is expected that a dose of 100–500 mg/kg/day is preferable, and for TSA the dosage could range from 10 to 100 mg/kg/day.

If given continuously, the compounds of the present invention are each typically administered by 1–4 injections per day or by continuous subcutaneous infusions, for example, using a mini-pump. An intravenous bag solution may also be employed. The key factor in selecting an appropriate dose is the result obtained.

For parenteral administration, in one embodiment, the compounds of the present invention are formulated generally by mixing each at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the compounds of the present invention each uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier may suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or non-ionic surfactants such as polysorbates, poloxamers, or PEG.

For oral pharmacological compositions such carrier material as, for example, water, gelatine, gums, lactose, starches, magnesium-stearate, talc, oils, polyalkene glycol, petroleum jelly and the like may be used. Such pharmaceutical preparation may be in unit dosage form and may additionally contain other therapeutically valuable substances or conventional pharmaceutical adjuvants such as preservatives, stabilising agents, emulsifiers, buffers and the like. The pharmaceutical preparations may be in conventional liquid forms such as tablets, capsules, dragees, ampoules and the like, in conventional dosage forms, such as dry ampoules, and as suppositories and the like.

The treatment with the present compounds may occur without, or may be imposed with, a dietary restriction such as a limit in daily food or calorie intake, as is desired for the individual patient.

A preferred embodiment of the present invention comprises locally administration of the compounds. Recently, site-specific drug delivery to the arterial wall has become a new strategy for the treatment of vascular diseases, including vessel restenosis following PTCA. These drug delivery systems include: (1) intravascular devices for site-specific (coronary artery) drug delivery comprising double-balloon catheters, porous balloon catheters, microporous balloon catheters, channel balloon catheters, balloon over stent catheters, hydrogel coated balloon catheters, iontophoretic balloon catheters and stent devices; (2) periadventitial and epicardial drug delivery devices, requiring surgical implantation, which include drug-eluting polymer matrices and a iontophoretic patch device; and (3) intramural injection of drug-eluting microparticles.

In addition, the compounds of the present invention are appropriately administered in combination with other treatments for combating or preventing stenosis.

The invention will be more fully understood by reference to the following examples. They should not, however, be construed as limiting the scope of the invention.

Experimental Section
Methods and Results

EXAMPLE 1
Preparation and Characterisation of the Compounds
a) Synthesis of the Novel Compounds Fatty acids with the heteroatom in variable positions were synthesised according to the general description for 3-substituted analogues (see below) with the following modification:

Alkyl-Hal was replaced by Alcanoic-Hal and HS—CHCOOR was replaced by alkyl-SH.

The following fatty acid analogues have been prepared and characterised:

| Compounds | Reactants | Melting-point (° C.) |
|---|---|---|
| Dodecanylthiobutanoic acid | 4-bromdbutanoic acid + dodecanylthiol | 54–55 |
| Decanylthiohexanoic acid | 6-brornohexanoic acid + decanylthiol | 50–51 |
| Octanylthiooctanoic acid | 8-bromooctanoic acid + octanylthiol | 39–40 |

Purification of products as described below. Purity >95%. Structure was verified by mass spectrometry.

b) The Synthesis of the 3-substituted Fatty Acid Analogues

The compounds used according to the present invention wherein the substituent $X_{i=3}$ is a sulphur atom or selenium atom may be prepared according to the following general procedure:

X is a sulphur atom:
The thio-substituted compound used according to the present invention may be prepared by the general procedure indicated below:

The sulphur-compound, namely, tetradecylthioaceticacid (TTA), $(CH_3-(CH_2)_{13}-S-CH_2-COOH$ was prepared as shown in EP-345.038.

X is a selenium atom:
the seleno-substituted compound used according to the present invention may be prepared by the following general procedure

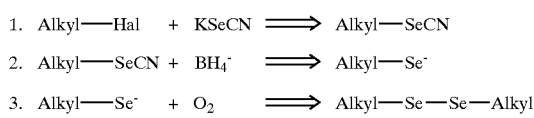

This compound was purified by carefully crystallisation from ethanol or methanol.

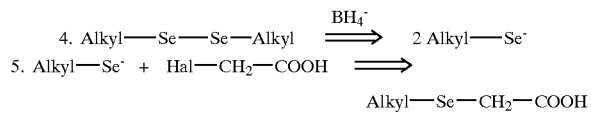

The final compound, e.g. when alkyl is tetradecyl, $(CH_3-(CH_2)_{13}-Se-CH_2-COOH$ (tetradecylselinioacetic acid (TSA)) can be purified by crystallisation from diethyl ether and hexane. This product may be fully characterised by NMR, IR and molecular weight determination.

The methods for the synthesis and isolation of these Sulphur and Selenium compounds, and the compound wherein X of formula I is Oxygen (O), Sulphur-I-oxide (SO) and Sulphurdioxide ($S_2$) are described in European Patent No. 345.038, and International Patent Application No. WO 97/03663.

EXAMPLE 2
Toxicity Study of TTA

A 28 days toxicity study in dogs according to GLP guidelines has been performed by Corning Hazleton (Europe), England. Oral administration of TTA at dose levels up to 500 mg/kg/day was generally well tolerated. Some lipid related parameters were lowered in the animals given high dosages. This is consistent with the pharmacological activity of TTA.

The dose level of 500 mg/kg/day also elicited body weight loss. There was no evidence of toxicity at dose levels of 50 or 500 mg/day/kg.

Tests for mutagenic activity have been performed by Covance Laboratories Limited, England. It was concluded that TTA and TSA did not induce mutations in strains of *Salmonella typhimurium* and *Escherichia coli*. Furthermore, TTA was not mutagenic when tested in mouse lymphoma cells and L5178Y.

The concentration of the compounds tested in *S. typhimurium* and *E. coli* were 3–1000 mg/plate (TTA) and 2–5000 mg/plate (TSA). In mouse lymphoma cells, L5178Y, the concentration was 2,5–50 mg/ml.

TSA and TSA were found not to be mutagenic in these tests. TSA and TTA have been tested for chromosomal aberrations in cultured Chinese hamster ovary cells and no aberrations were induced by the doses tested (12–140 mg/ml).

The compounds of the present invention are therefore potentially useful as pharmaceutical compounds in this respect.

EXAMPLE 3
Prevention of Restenosis in Rabbits Given TTA Orally

Fourteen Chinchilla (Chbb:CH) rabbits of either sex were randomised either to receive supplement with TTA fatty acids 800 mg daily (mean weight 3.6±0.09 kg) or to placebo (mean weight 3.5±0.47 kg).

The animals were pre-treated with TTA given as oral supplements, mixed with daily food pellets, for three weeks to ensure accumulation of the fatty acid analogues in the tissues.

The local ethical committee for animal care and use approved the experimental protocol.

TTA was synthesised as described in the method section. All other chemicals were from common commercial sources and were of reagent grade.

Angioplasty Procedure

After premedication with 0,5 ml fentanyl (0.315 mg/ml) and fluanisone (10 mg/ml) (Hypnorm®) intramuscularly, the rabbits were anaesthetised by administering diazepam 4 mg/kg intraperitoneally and maintained by additional 0.3–0.4 ml of a 1:1 mixture of Hypnorm® and diazepam, usually necessary once during the procedure.

After local infiltration of the skin by lignocaine (Xylocaine®) and surgical cut-down, the right carotid artery was cannulated by a 6F sheath. A bolus of 100 U/kg of heparin was administered intraarterially. Before the angioplasty, an angiography was performed in the frontal view by injecting 3 ml of ioxaglate (Hexabrix®) as contrast medium via a Berman® catheter.

An angioplasty balloon catheter (Express®) of 2.5 mm was positioned in the proximal part of each iliac artery and balloon angioplasty was performed with 2 balloon inflations at the same site in each artery, at 8 and 12 atmosphere for 30 seconds each to overstrech the artery. The balloon marker, on the middle of the 20 mm long balloon, was placed over the ilio-sacral joint, thus ensuring that the balloon was positioned at identical sites. Inflation was performed using a pressure manometer (Encore® 26 inflation device, Scimed, Boston Scientific corporation)

A further angiography was performed in the same frontal view as the first angiography to assure artery patency. The carotid artery was ligated and the skin was closed with ligatures. Buprenorfin 0.3 mg (Temgesic®) and penicillin were given subcutaneous once daily for the first days.

A follow-up angiography was performed in the same frontal view after 10 weeks, following the same procedure as indicated above, by using ioxaglate (Hexabrix®) as contrast medium. The sheath was now inserted in the left carotid artery. Intravascular ultrasound was performed to quantitate wall thickness and lumen diameter. After angiography a laparotomy was performed and the abdominal aorta was cannulated with an 18 G infusion-needle. The animals were euthanised by giving overdose pentobarbital intraarterially via the sheath in the left carotid artery. The iliac arteries were perfusion fixed by infusing 2% glutaraldehyde into the distal aorta at a pressure of 100 mmHg over 15 minutes, using a cannula in the inferior caval vein as efflux.

Quantitative Angiography

The frames with maximal opacification from baseline angiographies (before and after dilatation), as well as from the follow-up angiography were stored for subsequent quantitative analysis. Arterial diameter before and after dilatation as well as the balloon to artery ratio were measured. The minimal luminal diameter, reference diameter and stenosis were determined. All measurements were performed with a digital electronic calliper (Sandhill, model EC-1)(12). A balloon angioplasty catheter (Express® 2.5 mm), placed on the abdomen and dilated at 8 atmospheres (rated balloon diameter 2.5 mm) served for calibration. The results are given in table 2.

TABLE 1

Angiographic measurements

|  | before dilatation placebo | TTA | after dilatation placebo | TTA | control angiography placebo | TTA |
|---|---|---|---|---|---|---|
| diameter artery (mm) ($D_s$) | 1.85 ± 0.20 | 1.91 ± 0.18 | 2.36 ± 0.19 | 2.36 ± 0.19 | 1.08 ± 0.47 | 1.60 ± 0.26 |
| reference diameter (mm) ($D_r$) | 1.85 ± 0.20 | 1.91 ± 0.18 | 1.86 ± 0.30 | 1.80 ± 0.17 | 1.96 ± 0.21 | 2.07 ± 0.15 |
| dilatation/stenosis ($D_r - D_s$)/$D_r$ |  |  | −27.7 | −31.2 | 43.2 | 23.5 |
| acute gain (mm) |  |  | 0.51 ± 0.30 | 0.48 ± 0.22 |  |  |
| late loss |  |  |  |  | 1.28 ± 0.49 | 0.76 ± 0.38 |
| loss index |  |  |  |  | 3.22 ± 2.27 | 1.53 ± 0.46 |

Acute gain: minimal luminal diameter (MLD) post dilatation minus diameter artery before dilatation. Late loss: MLD post dilatation minus MLD at control angiography. Loss index: late loss divided by acute gain.

The results given in the table clearly demonstrate that the diameter of the arteries after the dilatation procedure are equal for the control and treated groups. However, at follow-up at six weeks the results indicate that the TTA has inhibited the decrease in artery diameter, and TTA is thus capable to prevent or reduce the formation of restenosis.

EXAMPLE 4
Prevention of Restenosis in Mini Pigs—Local Administration of TTA

Various local drug delivery systems have been developed to enable local application of pharmacological agents in conjunction with PTCA. In this study 20 minipigs were randomised to placebo or active treatment with the fatty acid analogue tetradecylthioacetic acid (TTA) via a Transport® multiphorous angioplasty balloon catheter. This catheter has a sleeve embracing the balloon and the drug is delivered through a separate lumen connected to the sleeve which has multiple holes.

Coronary balloon angioplasty injury using an oversized balloon was performed to the LAD or LCx followed by 3 bolus deliveries of 0.5 ml (0.33 mg/ml TTA) of active drug/placebo. Quantitative angiography as indicated in the preceding sections was performed before and after injury, and after 4 weeks follow-up. Subsequently the pigs were sacrificed, perfusion-fixed with glutaraldehyde and the vessels prepared for histology with computer assisted planimetry. Radiolabelled 1-$^{14}$C-TTA was administered locally in two extra pigs and confirmed the presence of active drug in the coronary arteries after 4 and 6 weeks.

The luminal diameter (mm) before, after and at follow-up (six weeks after balloon injury) is indicated in table 2.

TABLE 2

Luminal diameter (mm) before and after PTCA, and at follow-up

|  | before | after | at follow-up |
| --- | --- | --- | --- |
| placebo | 2.7 | 3.0 | 1.3 |
| TTA treated | 2.6 | 3.2 | 2.2 |

The maximal intimal thickness was unchanged in the treated group with respect to the placebo group.

Figure 2:
FIG. 2 shows an iliac artery from an animal given TTA, six weeks after balloon injury.

The results are also visualised in the appending FIGS. 1 and 2 which shows the Iliac artery 6 weeks after balloon injury for a control animal and a TTA administered animal, respectively.

TABLE 3

IVUS (intravascular ultrasound)

|  | Placebo | TTA |  |
| --- | --- | --- | --- |
| Area site mm$^2$ | 0.42 ± 0.086 | 0.61 ± 0.152 | p = 0.008 |
| Max. diameter site mm | 2.38 ± 0.311 | 2.87 ± 0.408 | p = 0.012 |
| Minimal diameter site mm | 2.25 ± 0.256 | 2.76 ± 0.381 | p = 0.005 |

The ICUS (intracoronary ultrasound) results were consistent with the angiography data.

Histology

The dilated segments of the iliac arteries were located by fluoroscopy, using the ilio-sacral joint as anatomical hallmark and dissected in block. Serial sections were processed and the segments were embedded in parafin. Cross sections were stained with hematoxylin-eosin and Verhoeff-van Gieson stains. All sections were evaluated for intima proliferation, interruption of the internal elastic lamina, the presence of luminal and intramural thrombus and for vessel area (data not shown).

EXAMPLE 5

Reduced Proliferation of Smooth Muscle Cells

Restenosis lesions may have an overgrowth of smooth muscle cells in the intiminal layer of the vessel, and we thus tested the effect of TTA on cultured muscle cells.

SMC are human smooth muscle cells available from American Type Culture Collection (Type 1999-CRL). The SMC cells were cultured in bottles (75 cm$^2$) in Ham's F12K medium. 24 hours after inoculation, the fatty acids and BSA in a molar ratio of 1:2.5 were added to the medium, i.e. to a final concentration of palmitic acid and TTA of 100 μM. After 3 and 6 days the cells were trypsinated, and the number of cells determined by using a light microscopy with counting chambers (Leitz Wetzler).

Figure 3:
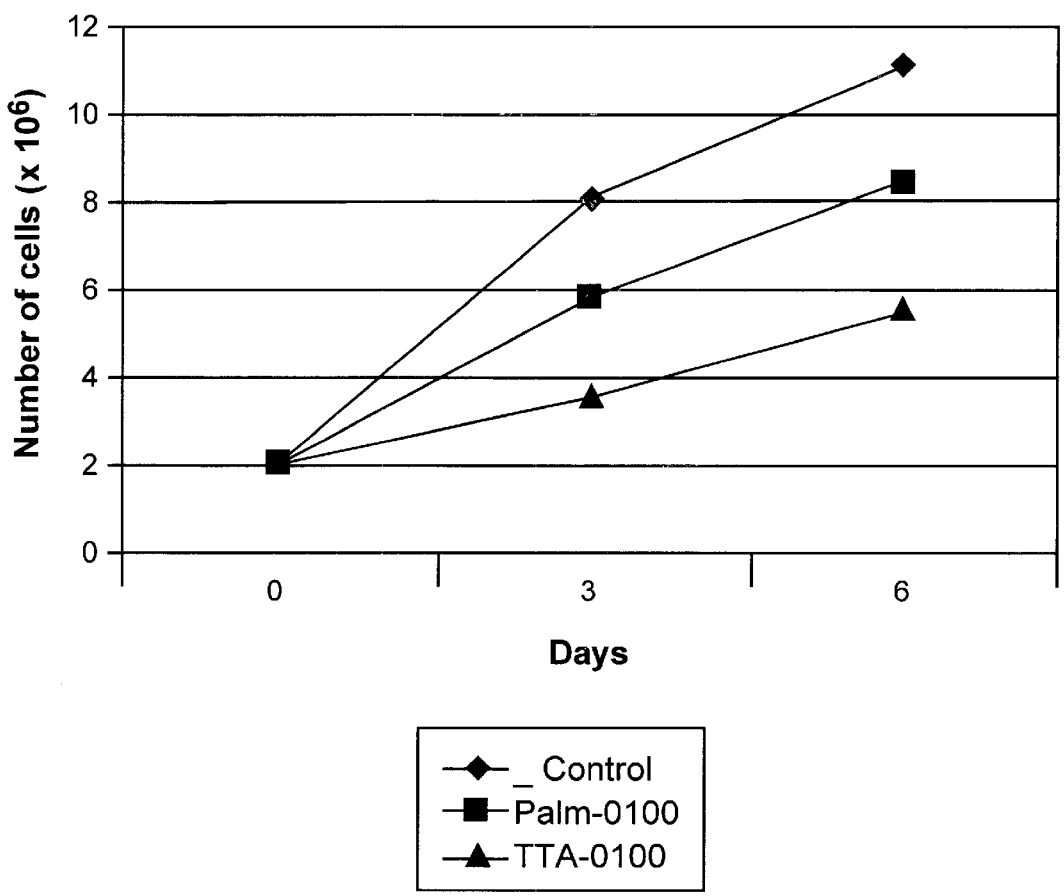
FIG. 3 shows the inhibiting effect of TTA on the growth of smooth muscle cells.

FIG. 3 shows the inhibiting effect of TTA on smooth muscle cells.

The inhibition of the proliferation of smooth muscle cells may be one of several mechanisms for the restenosis preventing effect of TTA.

EXAMPLE 6

TTA Reduces the Level of Plasma Homocysteine

Increased levels of homocysteine, i.e. hyperhomocysteinemia has been proposed to be associated with arterial diseases, and we thus measured the levels of homocysteine in plasma samples from Male Wistar rats given 300 mg TTA per kg body weight per day in 10 days.

Total plasma homocysteine was measured by a fully automated fluorescence assay. 30 μl plasma was reduced by 30 μl NaBH4/DMSO solution (6 mol/L). After 1,5 min 20 μl of the fluorescence reagent monobromobimane (25 mmol/L) in acetonitrile was added and allowed to react for 3 min. 20 μl of the sample was then immediately analysed with HPLC by injection on a strong cation-exchange column, and then by column switching into a cyclohexyl silica column. The SCX column was eluted isocratically and the CH column was eluted with a linear methanol gradient (17–35% in 5 min) in 20 mmol/L formate buffer. The homocysteine was eluted at a retention time of 4.5 min. The results are given in table 4.

TABLE 4

Plasma concentration of homocysteine

|  | Plasma concentration (μmol/L) |
| --- | --- |
| Control (CMC) | 10.6 ± 0.8 |
| TTA | 5.4 ± 1.0 |

What is claimed is:

1. A method for a therapeutic treatment and prophylaxes of restenosis in a mammal, said method comprising administering to a mammal to susceptible to a formation of resten therapeutically effective amount of at least one fatty acid analogue of the general formula (I)

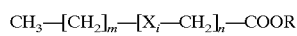

$$CH_3-[CH_2]_m-[X_i-CH_2]_n-COOR$$

wherein n is an integer from 1 to 12, and m is an integer from 0 to 23, and i is an odd number which indicates the position relative to COOR, and each $X_i$ is independently selected from the group consisting of O, S, SO, SO$_2$, Se, and CH$_2$, and R represents hydrogen or C$_1$–C$_4$ alkyl, with the proviso that at least one of the $X_i$ is not CH$_2$, or a salt, prodrug, or derivative thereof.

2. The method of claim 1, wherein the mammal is a human.

3. The method of claim 1, wherein m is greater than or equal to 13.

4. The method of claim 2, wherein $X_{i=3}$ is selected from the group consisting of O, S, SO, SO$_2$, and Se, and wherein $X_{i=5-25}$ is CH$_2$.

5. The method of claim 4, wherein $X_{i=3}$ is S.

6. The method of claim 4, wherein $X_{i=3}$ is Se.

7. The method of claim 1, wherein the at least one fatty acid analogue is administered such that its concentration is maintained substantially continuously in the blood of the mammal for the duration of the period of administration.

8. The method of claim 1, wherein the at least one fatty acid analogue is administered orally or locally.

9. The method of claim 1, wherein the restenosis is due to a graft or transplant procedure.

10. The method of claim 1, wherein the restenosis is due to angioplasty.

11. The method of claim 10, wherein the angioplasty is percutaneous transluminal coronary angioplasty (PTCA).

12. A method for lowering a concentration of homocysteine in plasma, comprising administering to a mammal an effective amount of at least one fatty acid analogue of the general formula (I)

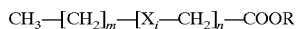

$$CH_3-[CH_2]_m-[X_i-CH_2]_n-COOR$$

wherein n is an integer from 1 to 12, and m is an integer from 0 to 23, and i is an odd number which indicates the position relative to COOR, and each $X_i$ is independently selected from the group consisting of O, S, SO, $SO_2$, Se, and $CH_2$, and R represents hydrogen or $C_1$–$C_4$ alkyl, with the proviso that at least one of the $X_i$ is not $CH_2$, or a salt, prodrug, or derivative thereof.

13. The method of claim 12, wherein the mammal is a human.

14. The method of claim 12, wherein m is greater than or equal to 13.

15. The method of claim 13, wherein $X_{i=3}$ is selected from the group consisting of O, S, SO, $SO_2$, and Se, and wherein $X_{i=5\text{-}25}$ is $CH_2$.

16. The method of claim 15, wherein $X_{i=3}$ is S.

17. The method of claim 15, wherein $X_{i=3}$ is Se.

18. The method of claim 12, wherein the at least one fatty acid analogue is administered such that its concentration is maintained substantially continuously in the blood of the mammal for the duration of the period of administration.

19. The method of claim 12, wherein the at least one fatty acid analogue is administered orally or locally.

* * * * *